(12) United States Patent
Lee et al.

(10) Patent No.: US 10,597,777 B2
(45) Date of Patent: Mar. 24, 2020

(54) PRECURSOR COMPOSITION CONTAINING GROUP IV ORGANIC COMPOUND AND METHOD FOR FORMING THIN FILM USING SAME

(71) Applicant: EUGENETECH MATERIALS CO., LTD., Suwon-si, Gyeonggi-do (KR)

(72) Inventors: Geun-Su Lee, Suwon-si (KR); Yeong-Min Lee, Hwaseong-si (KR)

(73) Assignee: EUGENETECH MATERIALS CO., LTD., Suwon-si, Gyeonggi-do (KR)

( * ) Notice: Subject to any disclaimer, the term of this patent is extended or adjusted under 35 U.S.C. 154(b) by 0 days.

(21) Appl. No.: 15/776,942

(22) PCT Filed: Nov. 1, 2016

(86) PCT No.: PCT/KR2016/012456
§ 371 (c)(1),
(2) Date: May 17, 2018

(87) PCT Pub. No.: WO2017/086630
PCT Pub. Date: May 26, 2017

(65) Prior Publication Data
US 2018/0347042 A1    Dec. 6, 2018

(30) Foreign Application Priority Data

Nov. 19, 2015  (KR) .................. 10-2015-0162796
Mar. 2, 2016   (KR) .................. 10-2016-0025179

(51) Int. Cl.
| | | |
|---|---|---|
| *H01L 21/02* | (2006.01) | |
| *C23C 16/455* | (2006.01) | |
| *C23C 16/40* | (2006.01) | |
| *C23C 16/06* | (2006.01) | |
| *C07F 5/06* | (2006.01) | |
| *C07F 7/30* | (2006.01) | |
| *C23C 16/02* | (2006.01) | |
| *C07F 17/00* | (2006.01) | |
| *C07F 5/00* | (2006.01) | |
| *C23C 16/34* | (2006.01) | |

(52) U.S. Cl.
CPC ........... *C23C 16/45536* (2013.01); *C07F 5/00* (2013.01); *C07F 5/066* (2013.01); *C07F 7/30* (2013.01); *C07F 17/00* (2013.01); *C23C 16/0218* (2013.01); *C23C 16/06* (2013.01); *C23C 16/34* (2013.01); *C23C 16/40* (2013.01); *C23C 16/405* (2013.01); *C23C 16/45553* (2013.01); *H01L 21/0228* (2013.01); *H01L 21/02178* (2013.01); *H01L 21/02181* (2013.01); *H01L 21/02189* (2013.01); *H01L 21/02194* (2013.01); *H01L 21/02205* (2013.01); *H01L 21/02271* (2013.01)

(58) Field of Classification Search
CPC ......... H01L 21/02178; H01L 21/02181; H01L 21/02189; H01L 21/02194; H01L 21/02205; H01L 21/02271; H01L 21/02274; H01L 21/0228; C07F 5/00; C07F 5/061; C07F 5/066; C07F 7/00; C07F 7/30; C07F 17/00; C07F 19/00; C23C 16/06; C23C 16/18; C23C 16/403; C23C 16/405; C23C 16/407
See application file for complete search history.

(56) References Cited

U.S. PATENT DOCUMENTS

| | | | | |
|---|---|---|---|---|
| 2007/0252244 | A1* | 11/2007 | Srividya | .................. C23C 16/40 257/635 |
| 2008/0032465 | A1* | 2/2008 | Ahn | ....................... C23C 16/308 438/142 |
| 2009/0091003 | A1* | 4/2009 | Lim | ......................... C23C 16/40 257/635 |
| 2015/0110958 | A1* | 4/2015 | Lansalot-Matras | ..... C23C 16/40 427/253 |
| 2017/0044664 | A1* | 2/2017 | Dussarrat | ............... C23C 16/405 |
| 2017/0117142 | A1* | 4/2017 | Lee | ............................ C07F 7/30 |

* cited by examiner

*Primary Examiner* — Stephen W Smoot
(74) *Attorney, Agent, or Firm* — Rabin & Berdo, P.C.

(57) ABSTRACT

The invention relates to a precursor composition containing a mixture of a Group IV organic compound represented by Formula 19 and any one compound selected from an organic aluminum compound represented by Formula 1, an organic gallium compound represented by Formula 7, or an organic germanium compound represented by Formula 16, and a method for forming a thin film by using the precursor composition.

39 Claims, No Drawings

PRECURSOR COMPOSITION CONTAINING GROUP IV ORGANIC COMPOUND AND METHOD FOR FORMING THIN FILM USING SAME

TECHNICAL FIELD

The present invention relates to a precursor composition containing a group IV organic compound and a method for forming a thin film using same, and more particularly, to a precursor composition containing a mixture of one compound selected from an organic aluminum compound, an organic gallium compound or an organic germanium compound with a group IV organic compound, and a method for forming a thin film using same.

BACKGROUND ART

In manufacturing semiconductor devices, thin films such as an aluminum-containing film, a gallium-containing film and a germanium-containing film are generally formed using a metal organic chemical vapor deposition (MOCVD) or an atomic layer deposition (ALD) process. According to the MOCVD deposition method, thin films such as an aluminum-containing film, a gallium-containing film and a germanium-containing film with high quality may be formed through a chemical vapor deposition method, and according to the ALD deposition method, thin films such as an aluminum-containing film, a gallium-containing film and a germanium-containing film with high uniformity may be formed, and these thin films may be controlled even up to the atomic units thereof.

In order to deposit thin films such as an aluminum-containing film, a gallium-containing film and a germanium-containing film with high quality through the MOCVD or ALD process, the selection of a precursor compound which is appropriate for a deposition process is very important. A precursor compound appropriate for the MOCVD or ALD process is required to have a high vapor pressure at a low temperature, be sufficiently thermally stable, and be a liquid compound having a low viscosity.

DISCLOSURE

Technical Problem

An aspect of the present invention is to provide a precursor composition including a mixture of one compound selected from an organic aluminum compound, an organic gallium compound or an organic germanium compound with a group IV organic compound, and a method for forming a thin film with high quality using same.

Another aspect of the present invention will become more apparent from the detailed description below.

Technical Solution

Embodiments of the present invention provide a precursor composition, the precursor composition comprises a mixture of one compound selected from an organic aluminum compound, an organic gallium compound and an organic germanium compound, with a group IV organic compound.

The organic aluminum compound is represented by the following <Formula 1>:

<Formula 1>

In <Formula 1>, $L_1$ and $L_2$ are each independently one selected from an alkyl group of 1 to 6 carbon atoms, and a cycloalkyl group of 3 to 6 carbon atoms, and $R_1$ and $R_2$ are each independently one selected from an alkyl group of 1 to 6 carbon atoms, and a cycloalkyl group of 3 to 6 carbon atoms.

The organic aluminum compound is represented by the following <Formula 2>:

<Formula 2>

The organic aluminum compound is represented by the following <Formula 3>:

<Formula 3>

The organic aluminum compound is represented by the following <Formula 4>:

<Formula 4>

The organic aluminum compound is represented by the following <Formula 5>:

<Formula 5>

The organic aluminum compound is represented by the following <Formula 6>:

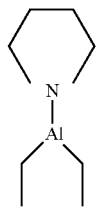

Formula 6

The organic gallium compound is represented by the following <Formula 7>:

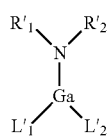

Formula 7

In <Formula 7>, $L'_1$ and $L'_2$ are each independently one selected from an alkyl group of 1 to 6 carbon atoms, and a cycloalkyl group of 3 to 6 carbon atoms, and $R'_1$ and $R'_2$ are each independently one selected from an alkyl group of 1 to 6 carbon atoms, and a cycloalkyl group of 3 to 6 carbon atoms.

The organic gallium compound is represented by the following <Formula 8>:

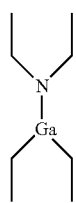

Formula 8

The organic gallium compound is represented by the following <Formula 9>:

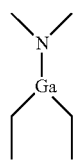

Formula 9

The organic gallium compound is represented by the following <Formula 10>:

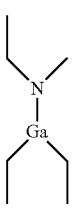

Formula 10

The organic gallium compound is represented by the following <Formula 11>:

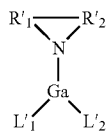

Formula 11

The organic gallium compound is represented by the following <Formula 12>:

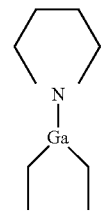

Formula 12

The organic germanium compound is represented by the following <Formula 13>:

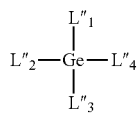

Formula 13

In <Formula 13>, $L''_1$, $L''_2$, $L''_3$ and $L''_4$ are each independently one selected from a hydrogen atom, an alkyl group of 1 to 5 carbon atoms, an aryl group of 5 to 8 carbon atoms, an alkylamine group of 1 to 6 carbon atoms, a dialkylamine group of 1 to 6 carbon atoms, an arylamine group of 6 to 12 carbon atoms, and an alkylsilylamine group of 2 to 6 carbon atoms.

The organic germanium compound is represented by the following <Formula 14>:

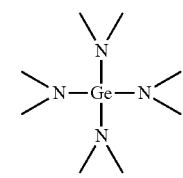

Formula 14

The organic germanium compound is represented by the following <Formula 15>:

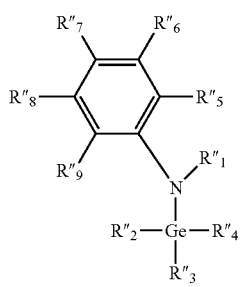

<Formula 15>

In <Formula 15>, $R''_1$, $R''_2$, $R''_3$ and $R''_4$ are each independently one selected from a hydrogen atom, an alkyl group of 1 to 6 carbon atoms, an alkylamine group of 1 to 6 carbon atoms, a dialkylamine group of 1 to 6 carbon atoms, an aryl group of 6 to 10 carbon atoms, an aralkyl group of 7 to 13 carbon atoms, and an alkylsilyl group of 2 to 10 carbon atoms, and $R''_5$ and $R''_9$ are each independently one selected from a hydrogen atom and an alkyl group of 1 to 6 carbon atoms.

The organic germanium compound is represented by the following <Formula 16>:

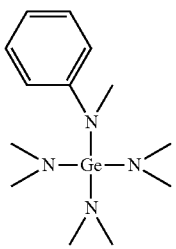

<Formula 16>

The organic germanium compound is represented by the following <Formula 17>:

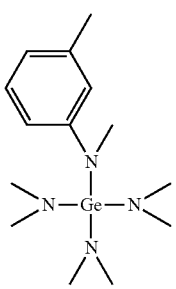

<Formula 17>

The group IV organic compound comprises a compound represented by the following <Formula 18>:

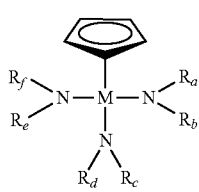

<Formula 18>

In <Formula 18>, M is selected from group IV compounds, and each of $R_a$ to $R_f$ may be the same or different, and is one selected from a hydrogen atom, an alkyl group of 1 to 6 carbon atoms, an aryl group of 6 to 10 carbon atoms, and an aralkyl group of 7 to 13 carbon atoms, where $R_a$ and $R_b$, $R_c$ and $R_d$, or $R_e$ and $R_f$ are interconnected, respectively, to form a cyclic amine group of 3 to 6 carbons together with a nitrogen atom combined therewith.

The group IV organic compound is a cyclopentadienyl zirconium(IV)-based compound represented by the following <Formula 19>:

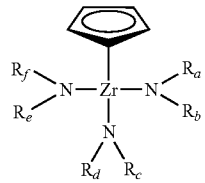

<Formula 19>

In <Formula 19>, $R_a$ to $R_b$ are the same as defined in <Formula 18>.

The group IV organic compound is a cyclopentadienyl hafnium (IV)-based compound represented by the following <Formula 20>.

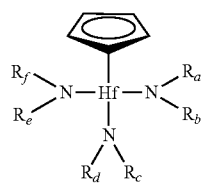

<Formula 20>

In <Formula 20>, $R_a$ to $R_b$ are the same as defined in <Formula 18>.

The group IV organic compound comprises a compound represented by the following <Formula 21>:

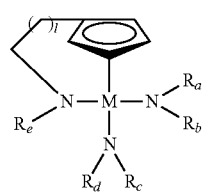

<Formula 21>

In <Formula 21>, M is selected from group IV elements, each of $R_a$ to $R_e$ may be the same or different, and is one selected from a hydrogen atom, an alkyl group of 1 to 6 carbon atoms, an aryl group of 6 to 10 carbon atoms, and an aralkyl group of 7 to 13 carbon atoms, where $R_a$ and $R_b$, $R_c$ and $R_d$, or $R_e$ are interconnected, respectively or from each other, to form a cyclic amine group of 3 to 6 carbons together with a nitrogen atom combined therewith, and 1 is an integer selected from an integer of 0 to 5.

The group IV organic compound is a cyclopentadienyl zirconium(IV)-based compound represented by the following <Formula 22>:

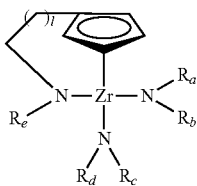

<Formula 22>

In <Formula 22>, $R_a$ to $R_e$ are the same as defined in <Formula 21>.

The group IV organic compound is a cyclopentadienyl hafnium (IV)-based compound represented by the following <Formula 23>:

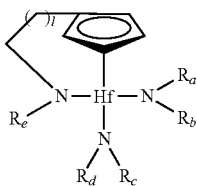

<Formula 23>

In <Formula 23>, $R_a$ to $R_e$ are the same as defined in <Formula 21>.

The group IV organic compound further comprises an aliphatic unsaturated compound represented by the following <Formula 24> or an aromatic compound represented by the following <Formula 25>:

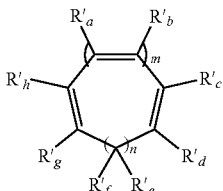

<Formula 24>

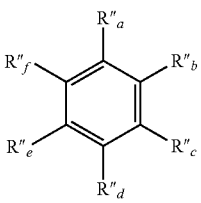

<Formula 25>

In <Formula 24>, each of $R'_a$ to R'h may be the same or different, and is selected from a hydrogen atom, an alkyl group of 1 to 6 carbon atoms, an aryl group of 6 to 12 carbon atoms, and an aralkyl group of 7 to 13 carbon atoms, m and n are each independently an integer selected from an integer of 0 to 10, and in <Formula 25>, each of $R''_a$ to $R''_f$ may be the same or different, and is selected from a hydrogen atom, an alkyl group of 1 to 6 carbon atoms, an aryl group of 6 to 12 carbon atoms, and an aralkyl group of 7 to 13 carbon atoms.

The group IV organic compound is obtained by mixing in a ratio of 1 mol to 3 mol of the compound represented by <Formula 18>; and 1 mol to 3 mol of the aliphatic unsaturated compound represented by <Formula 24> or the aromatic compound represented by <Formula 25>.

The group IV organic compound further comprises an aliphatic unsaturated compound represented by the following <Formula 24> or an aromatic compound represented by the following <Formula 25>:

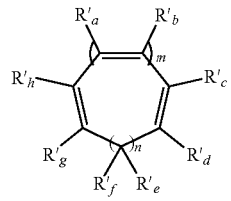

<Formula 24>

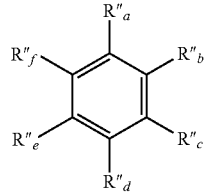

<Formula 25>

In <Formula 24>, each of $R'_a$ to R'h may be the same or different, and is selected from a hydrogen atom, an alkyl group of 1 to 6 carbon atoms, an aryl group of 6 to 12 carbon atoms, and an aralkyl group of 7 to 13 carbon atoms, m and n are each independently an integer selected from 0 to 10, and in <Formula 25>, each of $R''_a$ to $R''_f$ may be the same or different, and is selected from a hydrogen atom, an alkyl group of 1 to 6 carbon atoms, an aryl group of 6 to 12 carbon atoms, and an aralkyl group of 7 to 13 carbon atoms.

The group IV organic compound is obtained by mixing in a ratio of 1 mol to 3 mol of the compound represented by <Formula 21>; and 1 mol to 3 mol of the aliphatic unsaturated compound represented by <Formula 24> or the aromatic compound represented by <Formula 25>.

The precursor composition comprises 1-30 wt % of one compound selected from an organic aluminum compound, an organic gallium compound, and an organic germanium compound.

Embodiments of the present invention provide A method for forming a thin film, the method comprising forming a thin film on a substrate by a deposition method using the precursor composition according to any one of claims 1 to 29 as a precursor.

The deposition process is an atomic layer deposition (ALD) process or a chemical vapor deposition (CVD) process.

The deposition process is performed in a temperature range of 50-500° C.

Thermal energy, plasma or electrical bias is applied to a substrate during the deposition process.

The deposition process is performed by mixing the precursor composition with one or more carrier gases or dilution gases selected from argon (Ar), nitrogen (N2) helium (He) and hydrogen (H2), and by transferring the mixture gas to the substrate.

The thin film formed on the substrate is one of a zirconium aluminum film, a hafnium aluminum film, a zirconium gallium film, a hafnium gallium film, a zirconium germanium film or a hafnium germanium film.

The deposition process is performed by mixing the precursor composition with one or more reaction gases selected from water vapor ($H_2O$), oxygen ($O_2$) and ozone ($O_3$) and transferring the mixture gas to the substrate, or by transferring the reaction gas aside from the precursor composition to the substrate.

The thin film formed on the substrate is one of a zirconium aluminum oxide ($ZrAlO_x$) film, a hafnium aluminum oxide ($HfAlO_x$) film, a zirconium gallium oxide ($ZrGaO_x$) film, a hafnium gallium oxide ($HfAlO_x$) film, a zirconium germanium oxide ($ZrGeO_x$) film or a hafnium germanium oxide ($HfGeO_x$) film.

The deposition process is performed by mixing the precursor composition with one or more reaction gases selected from ammonia ($NH_3$), hydrazine ($N_2H_4$), nitrogen dioxide ($NO_2$) and nitrogen ($N_2$) plasmas and transferring the resultant mixture to the substrate, or by transferring the reaction gas aside from the precursor composition to the substrate.

The thin film formed on the substrate is one of a zirconium aluminum nitride ($ZrAlN_x$) film, a hafnium aluminum nitride ($HfAlN_x$) film, a zirconium gallium nitride ($ZrGaN_x$) film, a hafnium gallium nitride ($HfAlN_x$) film, a zirconium germanium nitride ($ZrGeN_x$) film or a hafnium germanium nitride ($HfGeN_x$) film.

The deposition process comprises: heating the substrate in a vacuum, activated or deactivated atmosphere at a temperature of 50-500° C.; introducing the precursor composition heated to a temperature of 20-100° C. onto the substrate; carrying out adsorption of the precursor composition onto the substrate to form an organic compound layer on the substrate; and applying thermal energy, plasma or electrical bias to the substrate to decompose an organic compound and to form a thin film on the substrate.

Advantageous Effects

The precursor composition according to an embodiment of the present invention includes a mixture of one compound selected from an organic aluminum compound, an organic gallium compound and an organic germanium compound with a group IV organic compound, and accordingly, if a thin film is deposited using the precursor composition according to an embodiment of the present invention, a group IV element aluminum-containing film, a group IV element gallium-containing film or a group IV element germanium-containing film may be effectively deposited only by supplying a single source via a single nozzle.

The group IV element aluminum-containing film, the group IV element gallium-containing film or the group IV element germanium-containing film, which is formed by the method for forming a thin film according to an embodiment of the present invention, has excellent thin film properties, thickness uniformity and step coverage properties.

BEST MODE

The present invention relates to a precursor composition and a method for forming a thin film using same, and hereinafter, embodiments of the present invention will be described using attached formulae. The embodiments of the present invention may include various modifications, and the scope of the present invention should not be construed to be limited to the embodiments described below.

In a semiconductor device, a plurality of thin films may be deposited on a substrate as necessary. Generally, in order to form a plurality of thin films on a substrate, a first precursor composition is supplied onto the substrate to form a first thin film, and a second precursor composition is supplied onto the substrate on which the first thin film is formed to form a second thin film on the first film.

In order to form a multi-layered thin film formed using a group IV element-containing film selected from an aluminum (Al)-containing film, a gallium (Ga)-containing film or a germanium (Ge)-containing film, one selected from an aluminum precursor compound, a gallium precursor compound or a germanium precursor compound and a group IV element precursor compound are required to be alternately supplied via each separate nozzle onto a substrate. The aluminum precursor compound, the gallium precursor compound or the germanium precursor compound has strong affinity with a group IV element precursor, and a reaction therebetween may be performed to form a precipitate on the substrate. In addition, the accurate control of the spraying amount of one precursor selected from the aluminum precursor compound, the gallium precursor compound or the germanium precursor compound, and the group IV element precursor is technically difficult. There are technical difficulties in accurately controlling the composition ratio of the group IV element with one element selected from aluminum, gallium or germanium in a multi-layered thin film.

Accordingly, the present invention intent to provide a precursor composition which is provided as a single precursor compound and is capable of forming a group IV element aluminum-containing film, a group IV element-containing gallium film or a group IV element germanium-containing film having excellent thin film properties, thickness uniformity and step coverage, and a method for forming a thin film using same.

Embodiments of the present invention provide a precursor composition, the precursor composition comprises a mixture of one compound selected from an organic aluminum compound, an organic gallium compound and an organic germanium compound, with a group IV organic compound.

The organic aluminum compound is represented by the following <Formula 1>:

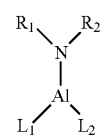

<Formula 1>

In <Formula 1>, $L_1$ and $L_2$ are each independently one selected from an alkyl group of 1 to 6 carbon atoms, and a cycloalkyl group of 3 to 6 carbon atoms, and $R_1$ and $R_2$ are each independently one selected from an alkyl group of 1 to 6 carbon atoms, and a cycloalkyl group of 3 to 6 carbon atoms.

The organic aluminum compound is represented by the following <Formula 2>:

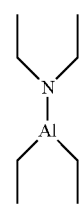

<Formula 2>

The organic aluminum compound is represented by the following <Formula 3>:

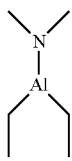

<Formula 3>

The organic aluminum compound is represented by the following <Formula 4>:

<Formula 4>

The organic aluminum compound is represented by the following <Formula 5>:

<Formula 5>

$$\begin{array}{c} R_1 - R_2 \\ \diagdown \diagup \\ N \\ | \\ Al \\ \diagup \diagdown \\ L_1 \quad L_2 \end{array}$$

The organic aluminum compound is represented by the following <Formula 6>:

<Formula 6>

The organic gallium compound is represented by the following <Formula 7>:

<Formula 7>

$$\begin{array}{c} R'_1 \quad R'_2 \\ \diagdown \diagup \\ N \\ | \\ Ga \\ \diagup \diagdown \\ L'_1 \quad L'_2 \end{array}$$

In <Formula 7>, $L'_1$ and $L'_2$ are each independently one selected from an alkyl group of 1 to 6 carbon atoms, and a cycloalkyl group of 3 to 6 carbon atoms, and $R'_1$ and $R'_2$ are each independently one selected from an alkyl group of 1 to 6 carbon atoms, and a cycloalkyl group of 3 to 6 carbon atoms.

The organic gallium compound is represented by the following <Formula 8>:

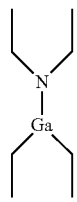

<Formula 8>

The organic gallium compound is represented by the following <Formula 9>:

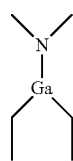

<Formula 9>

The organic gallium compound is represented by the following <Formula 10>:

<Formula 10>

The organic gallium compound is represented by the following <Formula 11>:

<Formula 11>

$$\begin{array}{c} R'_1 - R'_1 \\ \diagdown \diagup \\ N \\ | \\ Ga \\ \diagup \diagdown \\ L'_1 \quad L'_2 \end{array}$$

The organic gallium compound is represented by the following <Formula 12>:

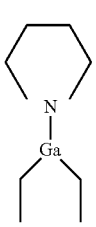

<Formula 12>

The organic germanium compound is represented by the following <Formula 13>:

<Formula 13>

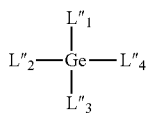

In <Formula 13>, L"₁, L"₂, L"₃ and L"₄ are each independently one selected from a hydrogen atom, an alkyl group of 1 to 5 carbon atoms, an aryl group of 5 to 8 carbon atoms, an alkylamine group of 1 to 6 carbon atoms, a dialkylamine group of 1 to 6 carbon atoms, an arylamine group of 6 to 12 carbon atoms, and an alkylsilylamine group of 2 to 6 carbon atoms.

The organic germanium compound is represented by the following <Formula 14>:

<Formula 14>

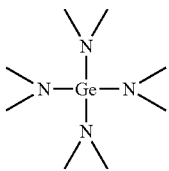

The organic germanium compound is represented by the following <Formula 15>:

<Formula 15>

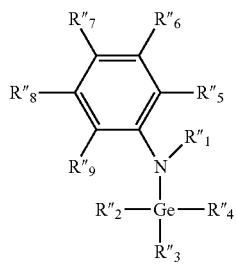

In <Formula 15>, R"₁, R"₂, R"₃ and R"₄ are each independently one selected from a hydrogen atom, an alkyl group of 1 to 6 carbon atoms, an alkylamine group of 1 to 6 carbon atoms, a dialkylamine group of 1 to 6 carbon atoms, an aryl group of 6 to 10 carbon atoms, an aralkyl group of 7 to 13 carbon atoms, and an alkylsilyl group of 2 to 10 carbon atoms, and R"₅ and R"₉ are each independently one selected from a hydrogen atom and an alkyl group of 1 to 6 carbon atoms.

The organic germanium compound is represented by the following <Formula 16>:

<Formula 16>

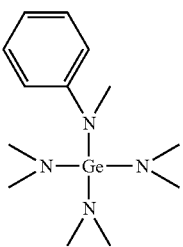

The organic germanium compound is represented by the following <Formula 17>:

<Formula 17>

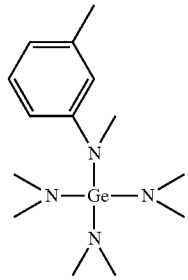

The organic germanium compound represented by the <Formula 13>~<Formula 17> exists in a liquid state at room temperature and has a small molecular size but high boiling point and excellent thermal stability. Therefore, when the organic germanium compound represented by the <Formula 13>~<Formula 17> is used as the germanium source, the temperature window can be narrowed in the deposition process, and the deposition rate, the step coverage can be improved by improving the deposition density, and the uniformity of the deposition about the germanium thin film.

The group IV organic compound comprises a compound represented by the following <Formula 18>:

<Formula 18>

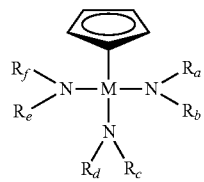

In <Formula 18>, M is selected from group IV compounds, and each of $R_a$ to $R_f$ may be the same or different, and is one selected from a hydrogen atom, an alkyl group of 1 to 6 carbon atoms, an aryl group of 6 to 10 carbon atoms, and an aralkyl group of 7 to 13 carbon atoms, where $R_a$ and $R_b$, $R_c$ and $R_d$, or $R_e$ and $R_f$ are interconnected, respectively, to form a cyclic amine group of 3 to 6 carbons together with a nitrogen atom combined therewith.

The group IV organic compound is a cyclopentadienyl zirconium(IV)-based compound represented by the following <Formula 19>:

<Formula 19>

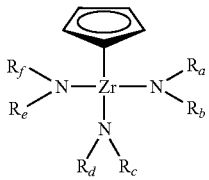

In <Formula 19>, $R_a$ to $R_b$ are the same as defined in <Formula 18>.

The group IV organic compound is a cyclopentadienyl hafnium (IV)-based compound represented by the following <Formula 20>:

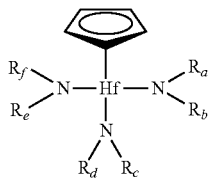

<Formula 20>

In <Formula 20>, $R_a$ to $R_b$ are the same as defined in <Formula 18>.

The group IV organic compound comprises a compound represented by the following <Formula 21>:

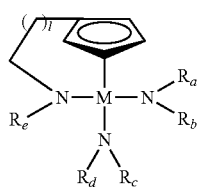

<Formula 21>

In <Formula 21>, M is selected from group IV elements, each of $R_a$ to $R_e$ may be the same or different, and is one selected from a hydrogen atom, an alkyl group of 1 to 6 carbon atoms, an aryl group of 6 to 10 carbon atoms, and an aralkyl group of 7 to 13 carbon atoms, where $R_a$ and $R_b$, $R_c$ and $R_d$, or $R_e$ are interconnected, respectively or from each other, to form a cyclic amine group of 3 to 6 carbons together with a nitrogen atom combined therewith, and l is an integer selected from an integer of 0 to 5.

The group IV organic compound is a cyclopentadienyl zirconium(IV)-based compound represented by the following <Formula 22>:

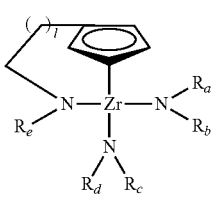

<Formula 22>

In <Formula 22>, $R_a$ to $R_e$ are the same as defined in <Formula 21>.

The group IV organic compound is a cyclopentadienyl hafnium (IV)-based compound represented by the following <Formula 23>:

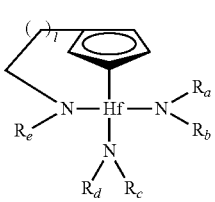

<Formula 23>

In <Formula 23>, $R_a$ to $R_e$ are the same as defined in <Formula 21>.

The group IV organic compound further comprises an aliphatic unsaturated compound represented by the following <Formula 24> or an aromatic compound represented by the following <Formula 25>:

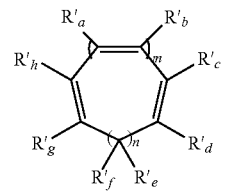

<Formula 24>

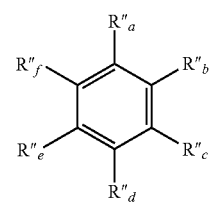

<Formula 25>

In <Formula 24>, each of $R'_a$ to R'h may be the same or different, and is selected from a hydrogen atom, an alkyl group of 1 to 6 carbon atoms, an aryl group of 6 to 12 carbon atoms, and an aralkyl group of 7 to 13 carbon atoms, m and n are each independently an integer selected from an integer of 0 to 10, and in <Formula 25>, each of $R''_a$ to $R''_f$ may be the same or different, and is selected from a hydrogen atom, an alkyl group of 1 to 6 carbon atoms, an aryl group of 6 to 12 carbon atoms, and an aralkyl group of 7 to 13 carbon atoms.

The group IV organic compound is obtained by mixing in a ratio of 1 mol to 3 mol of the compound represented by <Formula 18>; and 1 mol to 3 mol of the aliphatic unsaturated compound represented by <Formula 24> or the aromatic compound represented by <Formula 25>.

The group IV organic compound further comprises an aliphatic unsaturated compound represented by the following <Formula 24> or an aromatic compound represented by the following <Formula 25>:

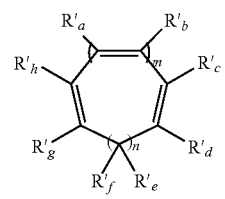

<Formula 24>

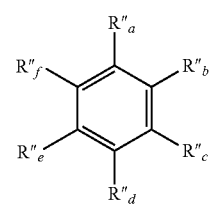

<Formula 25>

In <Formula 24>, each of $R'_a$ to R'h may be the same or different, and is selected from a hydrogen atom, an alkyl group of 1 to 6 carbon atoms, an aryl group of 6 to 12 carbon atoms, and an aralkyl group of 7 to 13 carbon atoms, m and n are each independently an integer selected from 0 to 10, and in <Formula 25>, each of R"$_a$ to R"$_f$ may be the same or different, and is selected from a hydrogen atom, an alkyl group of 1 to 6 carbon atoms, an aryl group of 6 to 12 carbon atoms, and an aralkyl group of 7 to 13 carbon atoms.

The group IV organic compound is obtained by mixing in a ratio of 1 mol to 3 mol of the compound represented by <Formula 21>; and 1 mol to 3 mol of the aliphatic unsaturated compound represented by <Formula 24> or the aromatic compound represented by <Formula 25>.

The precursor composition comprises 1-30 wt % of one compound selected from an organic aluminum compound, an organic gallium compound, and an organic germanium compound.

Embodiments of the present invention provide A method for forming a thin film, the method comprising forming a thin film on a substrate by a deposition method using the precursor composition according to any one of claims 1 to 29 as a precursor.

The deposition process is an atomic layer deposition (ALD) process or a chemical vapor deposition (CVD) process.

The deposition process is performed in a temperature range of 50–500° C.

Thermal energy, plasma or electrical bias is applied to a substrate during the deposition process.

The deposition process is performed by mixing the precursor composition with one or more carrier gases or dilution gases selected from argon (Ar), nitrogen (N2) helium (He) and hydrogen (H2), and by transferring the mixture gas to the substrate.

The thin film formed on the substrate is one of a zirconium aluminum film, a hafnium aluminum film, a zirconium gallium film, a hafnium gallium film, a zirconium germanium film or a hafnium germanium film.

The deposition process is performed by mixing the precursor composition with one or more reaction gases selected from water vapor (H$_2$O), oxygen (O$_2$) and ozone (O$_3$) and transferring the mixture gas to the substrate, or by transferring the reaction gas aside from the precursor composition to the substrate.

The thin film formed on the substrate is one of a zirconium aluminum oxide (ZrAlO$_x$) film, a hafnium aluminum oxide (HfAlO$_x$) film, a zirconium gallium oxide (ZrGaO$_x$) film, a hafnium gallium oxide (HfAlO$_x$) film, a zirconium germanium oxide (ZrGeO$_x$) film or a hafnium germanium oxide (HfGeO$_x$) film.

The deposition process is performed by mixing the precursor composition with one or more reaction gases selected from ammonia (NH$_3$), hydrazine (N$_2$H$_4$), nitrogen dioxide (NO$_2$) and nitrogen (N$_2$) plasmas and transferring the resultant mixture to the substrate, or by transferring the reaction gas aside from the precursor composition to the substrate.

The thin film formed on the substrate is one of a zirconium aluminum nitride (ZrAlN$_x$) film, a hafnium aluminum nitride (HfAlN$_x$) film, a zirconium gallium nitride (ZrGaN$_x$) film, a hafnium gallium nitride (HfAlN$_x$) film, a zirconium germanium nitride (ZrGeN$_x$) film or a hafnium germanium nitride (HfGeN$_x$) film.

The deposition process comprises: heating the substrate in a vacuum, activated or deactivated atmosphere at a temperature of 50-500° C.; introducing the precursor composition heated to a temperature of 20-100° C. onto the substrate; carrying out adsorption of the precursor composition onto the substrate to form an organic compound layer on the substrate; and applying thermal energy, plasma or electrical bias to the substrate to decompose an organic compound and to form a thin film on the substrate.

The germanium-containing film (GeO$_2$) formed by a method for forming a germanium-containing film according to an embodiment of the present invention, is a unstable film which is decomposed at a high temperature and reacts with water vapor (H$_2$O), and is not used as a single layer but is used for forming a germanium oxynitride (GeON) using nitrogen plasma or is used as a dopant of another oxides (ZrO$_2$, HfO$_2$, and the like).

Zirconium oxide (ZrO$_2$) which is used as the capacitor of DRAM is present in four structures including amorphous, monoclinic, tetragonal and cubic, and the capacitance thereof is changed according to the structure. The zirconium oxide (ZrO$_2$) with the tetragonal structure has a capacitance twice or more than other structures and has strong tendency to be present in the monoclinic structure which has a large volume at room temperature. Accordingly, the ratio of the tetragonal structure may be increased by doping an atom having a small cationic radius or an atom forming a tetragonal structure into a substrate. Also, germanium cations have a very small size than zirconium cations and are present in a tetragonal structure. Thus, a ZrGeO$_x$ film which is obtained by doping zirconium oxide into germanium cations, was secured to have a high dielectric constant than a zirconium oxide (ZrO$_2$) single film.

The present invention has been explained in detail with reference to embodiments, but other embodiments may be included. Accordingly, the technical idea and scope described in the claims below are not limited to the embodiments.

What is claimed is:

1. A precursor composition comprising a mixture of one compound selected from an organic aluminum compound, an organic gallium compound and an organic germanium compound, with a group IV organic compound, wherein the organic aluminum compound is represented by the following <Formula 1>:

<Formula 1> in <Formula 1>, L$_1$ and L$_2$ are each independently one selected from an alkyl group of 1 to 6 carbon atoms, and a cycloalkyl group of 3 to 6 carbon atoms, and R$_1$ and R$_2$ are each independently one selected from an alkyl group of 1 to 6 carbon atoms, and a cycloalkyl group of 3 to 6 carbon atoms.

2. The precursor composition of claim 1, wherein the organic aluminum compound is represented by the following <Formula 2>:

<Formula 2>

3. The precursor composition of claim 1, wherein the organic aluminum compound is represented by the following <Formula 3>:

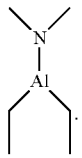

<Formula 3>

4. The precursor composition of claim 1, wherein the organic aluminum compound is represented by the following <Formula 4>:

<Formula 4>

5. The precursor composition of claim 1, wherein the organic aluminum compound is represented by the following <Formula 5>:

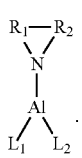

<Formula 5>

6. The precursor composition of claim 5, wherein the organic aluminum compound is represented by the following <Formula 6>:

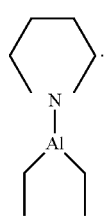

<Formula 6>

7. A precursor composition comprising a mixture of one compound selected from an organic aluminum compound, an organic gallium compound and an organic germanium compound, with a group IV organic compound, wherein the organic gallium compound is represented by the following <Formula 7>:

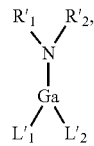

<Formula 7> in <Formula 7>, $L'_1$ and $L'_2$ are each independently one selected from an alkyl group of 1 to 6 carbon atoms, and a cycloalkyl group of 3 to 6 carbon atoms, and $R'_1$ and $R'_2$ are each independently one selected from an alkyl group of 1 to 6 carbon atoms, and a cycloalkyl group of 3 to 6 carbon atoms.

8. The precursor composition of claim 7, wherein the organic gallium compound is represented by the following <Formula 8>:

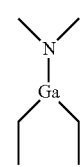

<Formula 8>

9. The precursor composition of claim 7, wherein the organic gallium compound is represented by the following <Formula 9>:

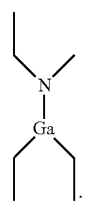

<Formula 9>

10. The precursor composition of claim 7, wherein the organic gallium compound is represented by the following <Formula 10>:

<Formula 10>

11. The precursor composition of claim 7, wherein the organic gallium compound is represented by the following <Formula 11>:

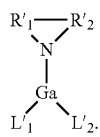

<Formula 11>

12. The precursor composition of claim 11, wherein the organic gallium compound is represented by the following <Formula 12>:

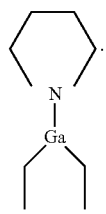

<Formula 12>

13. A precursor composition comprising a mixture of one compound selected from an organic aluminum compound, an organic gallium compound and an organic germanium compound, with a group IV organic compound, wherein the organic germanium compound is represented by the following <Formula 13>:

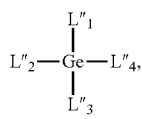

<Formula 13> in <Formula 13>, $L''_1$, $L''_2$, $L''_3$ and $L''_4$ are each independently one selected from a hydrogen atom, an alkyl group of 1 to 5 carbon atoms, an aryl group of 5 to 8 carbon atoms, an alkylamine group of 1 to 6 carbon atoms, a dialkylamine group of 1 to 6 carbon atoms, an arylamine group of 6 to 12 carbon atoms, and an alkylsilylamine group of 2 to 6 carbon atoms.

14. The precursor composition of claim 13, wherein the organic germanium compound is represented by the following <Formula 14>:

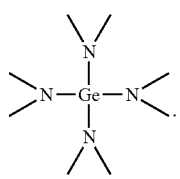

<Formula 14>

15. A precursor composition comprising a mixture of one compound selected from an organic aluminum compound, an organic gallium compound and an organic germanium compound, with a group IV organic compound, wherein the organic germanium compound is represented by the following <Formula 15>:

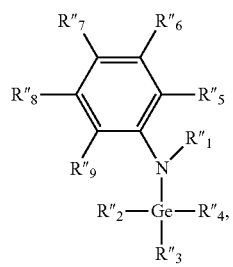

<Formula 15> in <Formula 15>, $R''_1$, $R''_2$, $R''_3$ and $R''_4$ are each independently one selected from a hydrogen atom, an alkyl group of 1 to 6 carbon atoms, an alkylamine group of 1 to 6 carbon atoms, a dialkylamine group of 1 to 6 carbon atoms, an aryl group of 6 to 10 carbon atoms, an aralkyl group of 7 to 13 carbon atoms, and an alkylsilyl group of 2 to 10 carbon atoms, and $R''_5$ and $R''_9$ are each independently one selected from a hydrogen atom and an alkyl group of 1 to 6 carbon atoms.

16. The precursor composition of claim 15, wherein the organic germanium compound is represented by the following <Formula 16>:

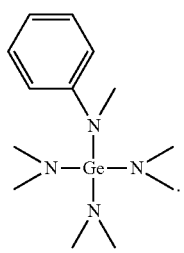

<Formula 16>

17. The precursor composition of claim 15, wherein the organic germanium compound is represented by the following <Formula 17>:

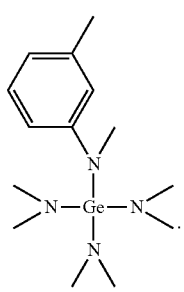

<Formula 17>

18. The precursor composition of claim 15, wherein the precursor composition comprises 1-30 wt % of one compound selected from the organic aluminum compound, the organic gallium compound, and the organic germanium compound.

19. A method for forming a thin film, the method comprising forming the thin film on a substrate by a deposition process using the precursor composition according to claim 15 as a precursor.

20. The method of claim 19, wherein the deposition process is an atomic layer deposition (ALD) process or a chemical vapor deposition (CVD) process.

21. The method of claim 19, wherein the deposition process is performed in a temperature range of 50-500° C.

22. The method of claim 19, wherein thermal energy, plasma or electrical bias is applied to a substrate during the deposition process.

23. The method of claim 19, wherein the deposition process is performed by mixing the precursor composition with one or more carrier gases or dilution gases selected from argon (Ar), nitrogen (N2) helium (He) and hydrogen (H2), and by transferring the mixture gas to the substrate.

24. The method of claim 23, wherein the thin film formed on the substrate is one of a zirconium aluminum film, a hafnium aluminum film, a zirconium gallium film, a hafnium gallium film, a zirconium germanium film or a hafnium germanium film.

25. The method of claim 19, wherein the deposition process is performed by mixing the precursor composition with one or more reaction gases selected from water vapor ($H_2O$), oxygen ($O_2$) and ozone ($O_3$) and transferring the mixture gas to the substrate, or by transferring the reaction gas aside from the precursor composition to the substrate.

26. The method of claim 25, wherein the thin film formed on the substrate is one of a zirconium aluminum oxide ($ZrAlO_x$) film, a hafnium aluminum oxide ($HfAlO_x$) film, a zirconium gallium oxide ($ZrGaO_x$) film, a hafnium gallium oxide ($HfAlO_x$) film, a zirconium germanium oxide ($ZrGeO_x$) film or a hafnium germanium oxide ($HfGeO_x$) film.

27. The method of claim 19, wherein the deposition process is performed by mixing the precursor composition with one or more reaction gases selected from ammonia ($NH_3$), hydrazine ($N_2H_4$), nitrogen dioxide ($NO_2$) and nitrogen ($N_2$) plasmas and transferring the resultant mixture to the substrate, or by transferring the reaction gas aside from the precursor composition to the substrate.

28. The method of claim 27, wherein the thin film formed on the substrate is one of a zirconium aluminum nitride ($ZrAlN_x$) film, a hafnium aluminum nitride ($HfAlN_x$) film, a zirconium gallium nitride ($ZrGaN_x$) film, a hafnium gallium nitride ($HfAlN_x$) film, a zirconium germanium nitride ($ZrGeN_x$) film or a hafnium germanium nitride ($HfGeN_x$) film.

29. The method of claim 19, wherein the deposition process comprises:
heating the substrate in a vacuum, activated or deactivated atmosphere at a temperature of 50-500° C.;
introducing the precursor composition heated to a temperature of 20-100° C. onto the substrate;
carrying out adsorption of the precursor composition onto the substrate to form an organic compound layer on the substrate; and
applying thermal energy, plasma or electrical bias to the substrate to decompose an organic compound and to form a thin film on the substrate.

30. A precursor composition comprising a mixture of one compound selected from an organic aluminum compound, an organic gallium compound and an organic germanium compound, with a group IV organic compound, wherein the group IV organic compound comprises a compound represented by the following <Formula 18>:

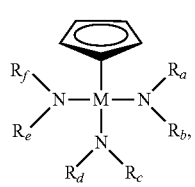

<Formula 18> in <Formula 18>, M is selected from group IV compounds, and each of $R_a$ to $R_f$ may be the same or different, and is one selected from a hydrogen atom, an alkyl group of 1 to 6 carbon atoms, an aryl group of 6 to 10 carbon atoms, and an aralkyl group of 7 to 13 carbon atoms, where $R_a$ and $R_b$, $R_c$ and $R_d$, or $R_e$ and $R_f$ are interconnected, respectively, to form a cyclic amine group of 3 to 6 carbons together with a nitrogen atom combined therewith.

31. The precursor composition of claim 30, wherein the group IV organic compound is a cyclopentadienyl zirconium (IV)-based compound represented by the following <Formula 19>:

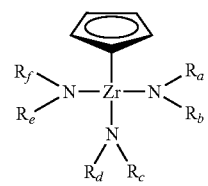

<Formula 19> in <Formula 19>, $R_a$ to $R_b$ are the same as defined in claim 30.

32. The precursor composition of claim 30, wherein the group IV organic compound is a cyclopentadienyl hafnium (IV)-based compound represented by the following <Formula 20>:

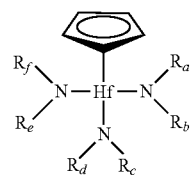

<Formula 20> in <Formula 20>, $R_a$ to $R_b$ are the same as defined in claim 30.

33. The precursor composition of claim 30, wherein the group IV organic compound further comprises an aliphatic unsaturated compound represented by the following <Formula 24> or an aromatic compound represented by the following <Formula 25>:

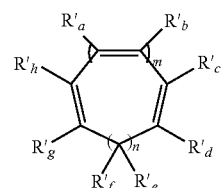

<Formula 24>

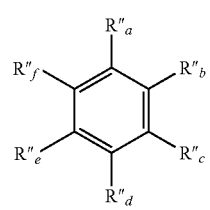

<Formula 25> in <Formula 24>, each of R'$_a$ to R'$_h$ may be the same or different, and is selected from a hydrogen atom, an alkyl group of 1 to 6 carbon atoms, an aryl group of 6 to 12 carbon atoms, and an aralkyl group of 7 to 13 carbon atoms, m and n are each independently an integer selected from an integer of 0 to 10, and in <Formula 25>, each of R"$_a$ to R"$_f$ may be the same or different, and is selected from a hydrogen atom, an alkyl group of 1 to 6 carbon atoms, an aryl group of 6 to 12 carbon atoms, and an aralkyl group of 7 to 13 carbon atoms.

34. The precursor composition of claim 33, wherein the group IV organic compound is obtained by mixing in a ratio of 1 mol to 3 mol of the compound represented by <Formula 18>; and 1 mol to 3 mol of the aliphatic unsaturated compound represented by <Formula 24> or the aromatic compound represented by <Formula 25>.

35. A precursor composition comprising a mixture of one compound selected from an organic aluminum compound, an organic gallium compound and an organic germanium compound, with a group IV organic compound, wherein the group IV organic compound comprises a compound represented by the following <Formula 21>:

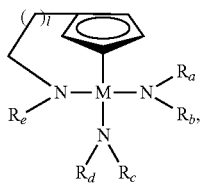

<Formula 21> in <Formula 21>, M is selected from group IV elements, each of R$_a$ to R$_e$ may be the same or different, and is one selected from a hydrogen atom, an alkyl group of 1 to 6 carbon atoms, an aryl group of 6 to 10 carbon atoms, and an aralkyl group of 7 to 13 carbon atoms, where R$_a$ and R$_b$, R$_c$ and R$_d$, or R$_e$ are interconnected, respectively or from each other, to form a cyclic amine group of 3 to 6 carbons together with a nitrogen atom combined therewith, and l is an integer selected from an integer of 0 to 5.

36. The precursor composition of claim 35, wherein the group IV organic compound is a cyclopentadienyl zirconium (IV)-based compound represented by the following <Formula 22>:

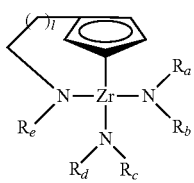

<Formula 22> in <Formula 22>, R$_a$ to R$_e$ are the same as defined in claim 35.

37. The precursor composition of claim 35, wherein the group IV organic compound is a cyclopentadienyl hafnium (IV)-based compound represented by the following <Formula 23>:

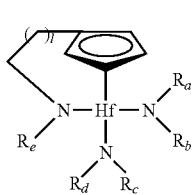

<Formula 23> in <Formula 23>, R$_a$ to R$_e$ are the same as defined in claim 35.

38. The precursor composition of claim 35, wherein the group IV organic compound further comprises an aliphatic unsaturated compound represented by the following <Formula 24> or an aromatic compound represented by the following <Formula 25>:

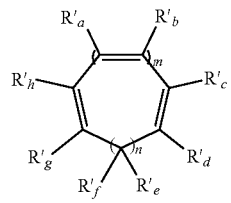

<Formula 24>

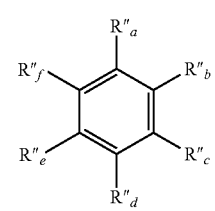

<Formula 25> in <Formula 24>, each of R'$_a$ to R'$_n$ may be the same or different, and is selected from a hydrogen atom, an alkyl group of 1 to 6 carbon atoms, an aryl group of 6 to 12 carbon atoms, and an aralkyl group of 7 to 13 carbon atoms, m and n are each independently an integer selected from 0 to 10, and in <Formula 25>, each of R"$_a$ to R"$_f$ may be the same or different, and is selected from a hydrogen atom, an alkyl group of 1 to 6 carbon atoms, an aryl group of 6 to 12 carbon atoms, and an aralkyl group of 7 to 13 carbon atoms.

39. The precursor composition of claim 38, wherein the group IV organic compound is obtained by mixing in a ratio of 1 mol to 3 mol of the compound represented by <Formula 21>; and 1 mol to 3 mol of the aliphatic unsaturated compound represented by <Formula 24> or the aromatic compound represented by <Formula 25>.

* * * * *